US010463302B1

(12) United States Patent
Ahmad et al.

(10) Patent No.: US 10,463,302 B1
(45) Date of Patent: Nov. 5, 2019

(54) LEADLESS ELECTROCARDIOGRAM MONITOR

(71) Applicant: THE ACCESS TECHNOLOGIES, Ottawa (CA)

(72) Inventors: Saif Ahmad, Kanata (CA); Atul Kumar Garg, Kanata (CA)

(73) Assignee: THE ACCESS TECHNOLOGIES, Ottawa (CA)

( * ) Notice: Subject to any disclaimer, the term of this patent is extended or adjusted under 35 U.S.C. 154(b) by 0 days.

(21) Appl. No.: 16/353,894

(22) Filed: Mar. 14, 2019

(30) Foreign Application Priority Data

Mar. 8, 2019 (CA) ..................................... 3036168

(51) Int. Cl.
*A61B 5/00* (2006.01)
*A61B 5/04* (2006.01)
(Continued)

(52) U.S. Cl.
CPC .......... *A61B 5/681* (2013.01); *A61B 5/04017* (2013.01); *A61B 5/0456* (2013.01);
(Continued)

(58) Field of Classification Search
CPC . A61B 5/861; A61B 5/04017; A61B 5/04085; A61B 5/0456; A61B 5/6828;
(Continued)

(56) References Cited

U.S. PATENT DOCUMENTS 5,289,824 A    3/1994  Mills et al.
7,460,899 B2   12/2008 Almen
(Continued)

FOREIGN PATENT DOCUMENTS

CN   108433718 A    8/2018
WO   WO2019042486 A1   3/2019

OTHER PUBLICATIONS

High resolution ambulatory electrocardiographic monitoring using wrist-mounted electric potential sensors; CJ Harland et al 2003 in Meas.Sci.Technol. 14 923.*
(Continued)

*Primary Examiner* — Paula J Stice
(74) *Attorney, Agent, or Firm* — Dorton & Willis, LLP; Ryan Willis

(57) ABSTRACT

This invention describes a wearable device related to electrocardiogram (ECG) monitoring technology. An ergonomically designed wireless smart band pair for continuous ECG monitoring and analysis is disclosed. The pair comprises a primary and a secondary smart band with integrated electrodes. When the smart bands are worn around the two wrists, the electrodes contact the skin. The primary smart band acquires biopotential data from the first wrist while the secondary smart band acquires biopotential data from the second wrist and sends it wirelessly to the primary smart band. The primary smart band processes biopotential data from both wrists to acquire high-fidelity ECG data as per Einthoven's law without the need for completing a circuit via leads and/or touching and holding auxiliary electrodes. The primary smart band analyzes the acquired ECG data in real-time and generates pertinent alarms. It also stores all ECG information locally and wirelessly transmits this information to external devices.

16 Claims, 16 Drawing Sheets

(51) Int. Cl.
*A61B 5/0456* (2006.01)
*A61B 5/0408* (2006.01)
*A61B 5/046* (2006.01)
*A61B 5/044* (2006.01)

(52) U.S. Cl.
CPC ........ *A61B 5/04085* (2013.01); *A61B 5/6824* (2013.01); *A61B 5/0006* (2013.01); *A61B 5/044* (2013.01); *A61B 5/046* (2013.01); *A61B 5/6823* (2013.01); *A61B 5/7225* (2013.01)

(58) Field of Classification Search
CPC ....... A61B 5/0006; A61B 5/044; A61B 5/046; A61B 5/6823
See application file for complete search history.

(56) References Cited

U.S. PATENT DOCUMENTS

| | | |
|---|---|---|
| 7,894,888 B2 | 2/2011 | Chan et al. |
| 8,527,038 B2 | 9/2013 | Moon et al. |
| 9,655,537 B2 | 5/2017 | Bardy et al. |
| 9,706,922 B2 | 7/2017 | Cao |
| 9,844,340 B2 | 12/2017 | Fish et al. |
| 9,955,887 B2 | 5/2018 | Hughes et al. |
| 10,045,708 B2 | 8/2018 | Dusan |
| 2011/0319777 A1 | 12/2011 | Mehrotra et al. |
| 2016/0028269 A1* | 1/2016 | Miller .................... H02J 50/10 455/573 |
| 2016/0317067 A1* | 11/2016 | Lee ....................... A61B 5/1118 |
| 2017/0020444 A1* | 1/2017 | Lurie ..................... A61B 5/486 |
| 2017/0055869 A1 | 3/2017 | Shin et al. |
| 2018/0345078 A1 | 12/2018 | Blahnik et al. |

OTHER PUBLICATIONS

Canadian Patent Office, "Examination Report", in published Canadian Patent Application 3,036,168, dated Jun. 14, 2019, 4 pp.

* cited by examiner

LEADLESS ELECTROCARDIOGRAM MONITOR

CROSS REFERENCE TO RELATED APPLICATIONS

The present application claims the priority under 35 U.S.C. § 119 to Canadian Patent Application Serial No. 3,036,168, titled, "LEADLESS ELECTROCARDIOGRAM MONITOR," filed Mar. 8, 2019, the disclosure of which is incorporated herein by reference.

TECHNICAL FIELD

In general, this invention relates to electrocardiogram (ECG) monitoring in humans with wearable technology, and in particular to continuous and unobtrusive ECG monitoring utilizing a pair of ergonomically designed wireless smart bands that the user wears around the left and right wrists.

BACKGROUND

A regular ECG test is an essential diagnostic tool that characterizes the heart's activity at a given point in time. Abnormal heart rhythms and cardiac symptoms may however appear, disappear, and reappear over time. Consequently, point-in-time ECG tests may miss critical cardiac anomalies, thereby leading to an increased risk of morbidity and mortality.

It is therefore important to monitor ECG continuously in at-risk patients as they go about their normal activities. Quite often, serious heart conditions like atrial fibrillation (AF), cardiomyopathy, and coronary heart disease are diagnosed with continuous ECG monitoring. This allows for timely clinical interventions like medication and cardiac surgery that reduce adverse outcomes like stroke and heart attack, thereby saving lives.

In clinical practice, it is common to undertake continuous ECG monitoring using a Holter system that can generally record 24-48 hours of cardiac data. The Holter is a small wearable biopotential measurement device comprising several ECG leads. These ECG leads are snapped on to sticky gel electrodes that are attached at various locations on the patient's chest. A Holter monitoring system is inconvenient and obtrusive due to the sticky gel chest electrodes that often cause discomfort and the unwieldy leads that hang between the electrodes and the Holter unit.

Recently, Medtronic has developed and marketed a leadless Holter system (SEEQ™) in the form of an adhesive chest strip (~4.5" long, ~2.0" wide, and ~0.6" thick) for continuous ECG monitoring. Though leadless, this monitor is awkward and uncomfortable because it uses sticky chest electrodes and it is too bulky to be attached to the chest.

Various kinds of belts that can be worn around the chest for continuous ECG monitoring are available in the market today. Many of these ECG chest belt systems are leadless and employ dry reusable electrodes. Still, these ECG belts need to be worn under clothing and are often quite tight around the chest, causing difficulty and uneasiness to the wearer.

Currently, continuous ECG monitoring technology comes with a number of problems and encumbrances. These include discomfort, uneasiness, sleep disruptions, difficulty in carrying out day-to-day activities, and inability to undertake long-term monitoring (for example, monitoring for days, months, and years).

With the advent of newer generation wearables like smartwatches, attempts have been made to integrate ECG monitoring into a smartwatch. For example, Apple has provided dry ECG electrodes on the backplate of a smartwatch (left-side electrodes) and a second set of electrodes on the smartwatch rim (right-side electrodes). A user has to wear the smartwatch on one wrist so that the electrodes underneath touch the wrist. Additionally, the user has to touch the second set of electrodes on the smartwatch rim with his/her other hand so that the heart lies in-between the left-side (backplate) and right-side (rim) electrodes that are electrically connected to signal amplification/conditioning circuitry inside the smartwatch. The quality of ECG data acquired in this manner is generally satisfactory. However, the main limitation is that the user has to touch and hold a second set of electrodes on the smartwatch with his/her other hand for monitoring ECG data. As a result, this system only provides an on demand 30 seconds of ECG monitoring, and not continuous and/or long-term ECG monitoring.

To avoid touching a second set of electrodes with the other hand and to accomplish leadless continuous ECG monitoring, attempts have been made to develop wearable single upper limb ECG systems.

Prior art has proposed the use of single arm wearable devices for leadless ECG monitoring. These systems comprise an upper arm band with more than one electrode on the underside that come in contact with the arm when the band is worn. The electrodes are interfaced with an amplification and control unit that may be affixed to the outer surface of the band. Single arm ECG systems have produced mixed results for a diverse population. The ECG signal acquired by these systems is often noisy, unreliable, and unusable, more so for women and older people.

Based on the principles of single arm ECG systems, other prior art has also proposed leadless ECG monitoring employing wearable single wrist systems. The quality and fidelity of data acquired by single wrist ECG systems has not been properly tested and/or verified. Intuitively, a single wrist ECG system will produce noisier and weaker signals as compared to a single arm ECG system. This is because the wrist is physically farther away from the heart as compared to the upper arm, thus resulting in greater impedance to the flow of electrical charge from the heart to the wrist electrodes.

INTRODUCTION TO THE INVENTION

In one aspect of the present invention there is disclosed a wearable device related to ECG monitoring technology. The wearable device comprises a pair of ergonomically designed wireless smart bands that are worn around the left and right wrists for unobtrusive continuous leadless ECG data monitoring and analysis. Both smart bands in the described pair are provided with dry reusable ECG electrodes on their underside. The electrodes in each smart band are interfaced with biopotential measurement hardware and software inside that smart band. Moreover, the hardware and software inside the two smart bands enables seamless wireless communication between them. When the two smart bands are worn on both hands, their respective electrodes come in contact with the left and right side of the body. With this configuration, the two smart bands independently measure biopotential on the left and right side of the body and wirelessly share/process this information to acquire/analyze high-fidelity ECG data. Thus, the wireless smart band pair accomplishes ECG data monitoring and analysis as per Einthoven's law without the need for physically completing a circuit via leads and/or touching and holding auxiliary electrodes.

The two smart bands in the described pair are alluded to as a primary smart band and a secondary smart band. Both the primary and secondary smart bands preferably comprise electrodes, ECG amplification/conditioning circuitry, a microcontroller, a wireless transceiver, and a rechargeable battery. The primary smart band can be additionally provided with memory and a touchscreen display. Both the primary and secondary smart bands preferably have wireless charging capabilities and can be charged on a twin wireless charging unit.

In one embodiment, both primary and secondary smart bands are provided with three ECG strip electrodes on their underside to maximize the electrode surface area and enhance connectivity around the wrist to obtain high-quality ECG signal. Each of the three strip electrodes can be arranged to have a rigid section on the smart band backplate and a flexible section along the underside of the smart band straps. In one example, the rigid electrodes are made of silver while the flexible electrodes are made of conductive fabric.

In one example, in both smart bands, the first strip is a right-side electrode and the second strip is a left-side electrode connected to a biopotential amplifier while the third strip is a ground electrode. In another example, in both smart bands, the right-side and left-side strip electrodes remain unchanged while the third strip is a right leg drive (RLD) electrode to reduce common mode noise and augment ECG signal quality. In yet another example, in both smart bands, the right-side and left-side strip electrodes remain unchanged while the third strip in the secondary smart band is a ground electrode and the third strip in the primary smart band is an RLD electrode for enhancing ECG data quality.

In one example, the primary smart band is worn around the left wrist while the secondary smart band is worn around the right wrist. With this setup, the primary smart band acquires biopotential data from the left side of the body. Simultaneously, the secondary smart band acquires biopotential data from the right side of the body and transmits this information wirelessly to the primary smart band. Biopotential information from the left and right side of the body is processed inside the primary smart band using a variety of methods to acquire high-fidelity ECG signal.

In one example, the biopotential data from both smart bands is sent directly to the microcontroller inside the primary smart band for processing and obtaining an ECG signal. In another example, the biopotential data from both smart bands is first sent to a differential amplifier for further amplification/conditioning and then to the microcontroller inside the primary smart band for processing and obtaining an ECG signal.

In a further embodiment, inside each smart band, a digital switch can be provided between each of the three strip electrodes and the associated signal amplification/conditioning circuitry, resulting in three digital electrode switches inside each smart band. These electrode switches allow various electrode configurations to be evaluated for enhancing ECG data quality. This feature is useful for device testing and calibration whereby an optimum electrode configuration that results in best ECG signal quality can be readily determined. In one example, all three electrodes, namely, right, left, and RLD of the primary smart band are switched on while only right and left electrodes of the secondary smart band are switched on.

In a further aspect, the microcontroller inside the primary smart band analyzes acquired ECG data in real-time to compute parameters like heart rate (HR) and heart rate variability (HRV) and to generate alerts when these parameters are out of range. For example, if HRV is above a given threshold, an AF alert is generated. The primary smart band displays real-time ECG waveform data along with metrics like HR and HRV and any alerts that are generated. The onboard memory in the primary smart band stores all ECG-related information. The primary smart band can also have the functionality to send all acquired ECG data and related information wirelessly to a smartphone, personal computer (PC), tablet, or directly to a cloud server where it can be further processed/analyzed.

Though this invention is described as related to a pair of wearable smart bands that are attached to a user's left and right wrists, the underlying design and principle of the invention can be extended to a pair of wearables that can be attached at any location along the two upper limbs and/or even the two lower limbs. One example comprises a primary smart band worn around the wrist and a secondary smart band worn around the upper arm of the other hand. Another example comprises both primary and secondary smart bands worn around the two upper arms. Yet another example comprises a primary smart band worn around the wrist and a secondary smart band worn around the ankle of the other leg. It will be appreciated that the smart band could be a smartwatch or any other similar wearable.

This invention fulfills the theoretical underpinnings of electrocardiography and Einthoven's law such that biopotential is measured on the left and right sides of the body with the heart in-between utilizing a pair of wirelessly synced wearables (for example, smart bands, smartwatches, and/or any combination thereof) that process all information to acquire high-fidelity single-lead ECG waveform data.

In one aspect of the present invention there is provided an electrocardiogram monitor comprising a primary wearable smart band having electrodes that are configured to contact skin of a user and measure a first biopotential, a secondary wearable smart band having electrodes that are configured to contact the skin of the user and measure a second biopotential, and a microcontroller in wireless communication with the primary smart band and the secondary smart band, wherein the microcontroller processes the first biopotential and second biopotential to determine an ECG signal.

DETAILED DESCRIPTION

Figure 1:
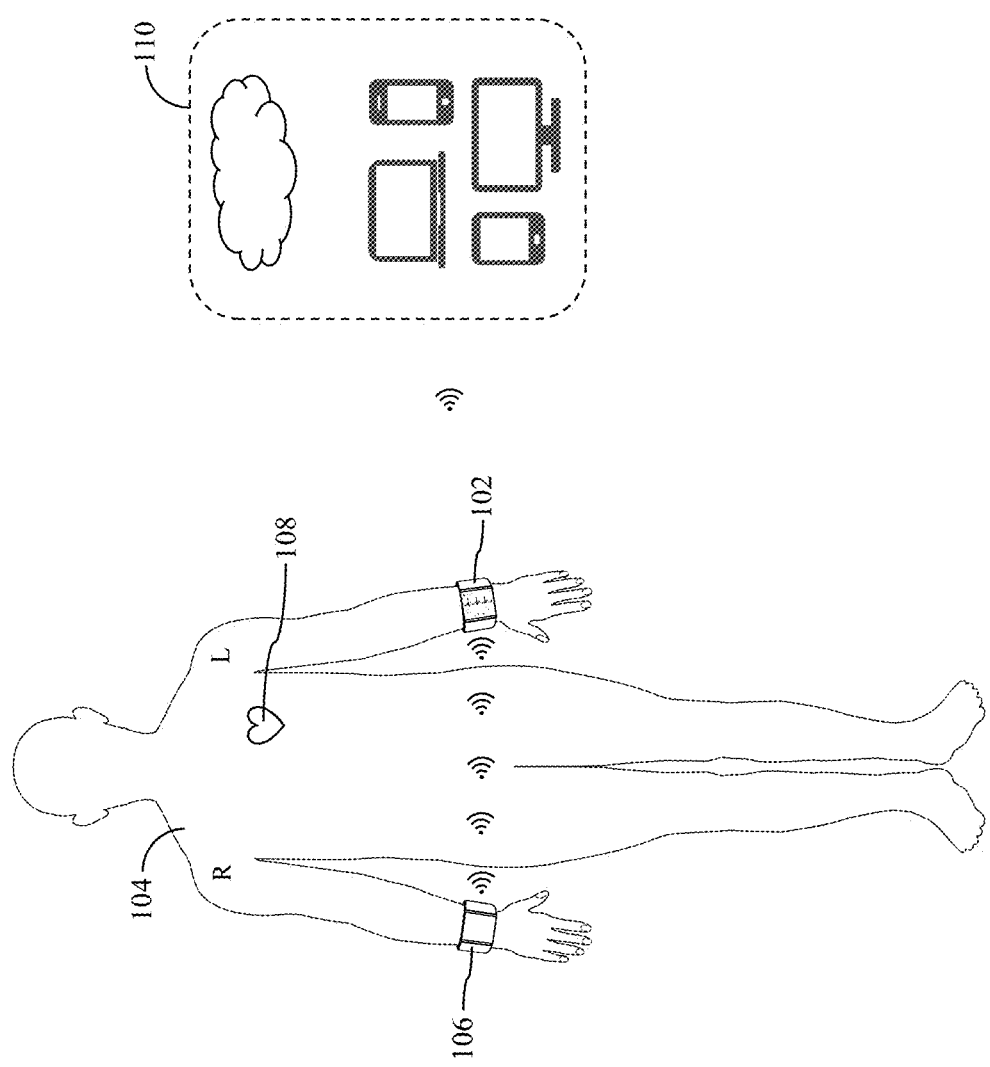
FIG. 1 illustrates an exemplary attachment of the wireless smart band pair on a user for continuous leadless ECG monitoring along with external devices to which data is wirelessly transmitted.

A preferred embodiment of the present invention will be set forth in detail with reference to the drawings, in which like reference numerals refer to like elements or method steps throughout.

FIG. 1 illustrates an exemplary attachment of the wireless smart band pair on a user for continuous leadless ECG monitoring along with external devices to which data is wirelessly transmitted. In this example, the primary smart band 102 is worn by the user 104 around the left wrist whereas the secondary smart band 106 is worn around the right wrist. The heart 108 is shown inside the chest cavity positioned slightly towards the left. The secondary smart band 106 worn around the right wrist measures the right-side biopotential by virtue of the electrodes provided on its underside (not shown) and sends this information wirelessly to the primary smart band 102 worn around the left wrist. Simultaneously, the primary smart band 102 worn around the left wrist measures the left-side biopotential by virtue of the electrodes provided on its underside (not shown) and combines/processes this information with the wirelessly received right-side biopotential information to acquire high-fidelity ECG waveform data. The primary smart band 102 analyzes the acquired ECG data, stores all information locally, and also transmits this information wirelessly to remote devices 110 like smartphones, laptops, tablets, and cloud databases for storage and further analysis. It will be apparent to those skilled in the art that the primary 102 and secondary 106 smart bands can also be swapped between the two hands to acquire ECG data in a manner similar to the one described above. That is, the primary smart band 102 can be also worn around the right wrist and the secondary smart band 106 can also be worn around the left wrist for continuous leadless ECG monitoring as outlined in the invention.

Figure 2C:
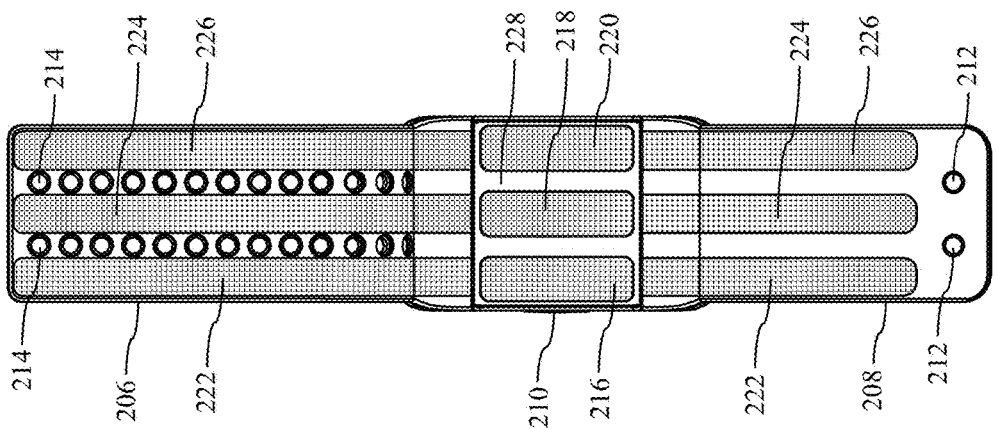
FIGS. 2A-2C illustrate the front, side, and back of the primary smart band showing the touchscreen display along with the rigid/flexible strip electrodes and clasping studs/holes.
Figure 2B:
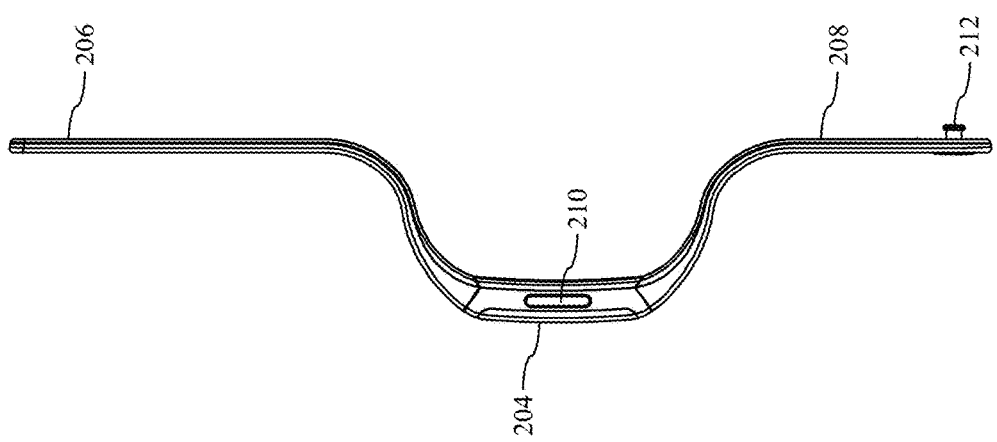
Figure 2A:
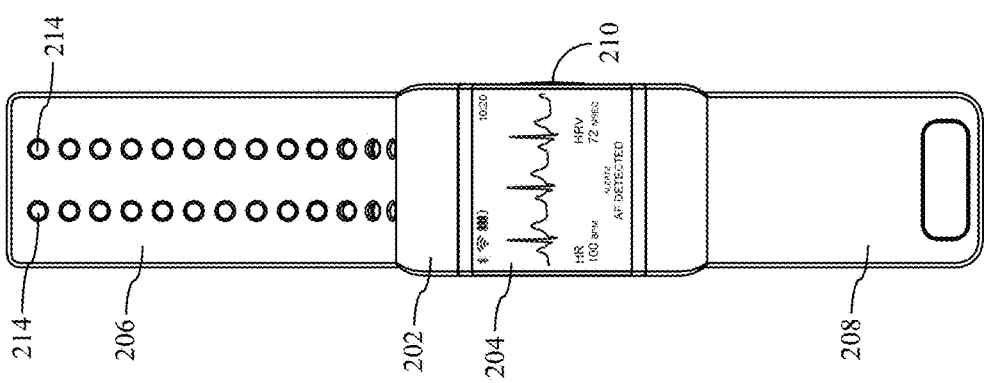

FIGS. 2A-2C illustrate one embodiment of the front, side, and back of the primary smart band showing the touchscreen display along with the rigid/flexible strip electrodes and clasping studs/holes. The primary smart band comprises an enclosure 202 made of stainless steel, a touchscreen display 204, upper 206 and lower 208 straps made of flexible rubber, and an on/off button 210. Studs 212 made of hard rubber and corresponding holes 214 are provided on the primary smart band straps for clasping it snugly around the wrist. It will be appreciated that while two sets of studs 212 and holes 214 are shown, a single set, multiple sets or other arrangements could be used instead. It will also be appreciated that the display 204 could be a plain display that is not a touchscreen.

Three rigid strip electrodes 216, 218, 220 and three flexible strip electrodes 222, 224, 226 are provided on the underside of the primary smart band. The three rigid strip electrodes 216, 218, 220 are embedded in the primary smart band backplate 228 that is made of plastic. The three flexible strip electrodes 222, 224, 226 are embedded in the upper 206 and lower 208 straps of the smart band. Each of the three rigid 216, 218, 220 and flexible 222, 224, 226 strip electrodes are electrically connected inside the primary smart band. That is rigid strip electrode 216 is connected to flexible strip electrode 222, rigid strip electrode 218 is connected to flexible strip electrode 224, and rigid strip electrode 220 is connected to flexible strip electrode 226. In one example, the rigid strip electrodes 216, 218, 220 are made of silver while the flexible strip electrodes 222, 224, 226 are made of silver foil. In another example, the rigid strip electrodes 216, 218, 220 are made of chrome-plated steel while the flexible strip electrodes 222, 224, 226 are made of conductive fabric. Those skilled in the art will appreciate that a variety of conductive materials can be used to fabricate the rigid and flexible strip electrodes described in this invention.

In one example, the approximate dimensions of the primary smart band enclosure 202 are 43.0 mm (length)×42.0 mm (width)×9.5 mm (height). The width of the straps 206, 208 is approximately 41.0 mm and closely matches the length of the smart band enclosure 202. The approximate width of the rigid 216, 218, 220 and flexible 222, 224, 226 strip electrodes is 8.5 mm and the approximate separation between them is 5.5 mm. In this example, the 5.5 mm gap between the flexible strip electrodes 222, 224, 226 conveniently allows for the primary smart band clasping studs 212 and holes 214 to be provided within this gap. The approximate weight of such a primary smart band is 40 g.

Figure 3C:
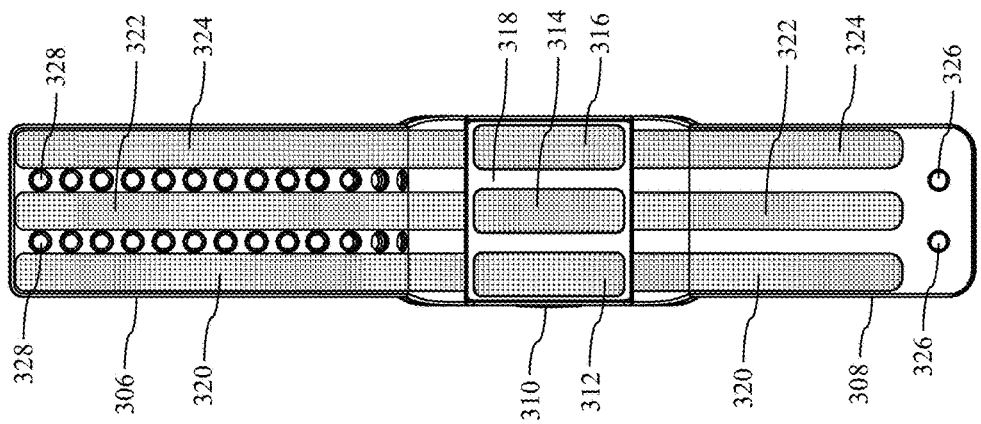
FIGS. 3A-3C illustrate the front, side, and back of the secondary smart band showing the front cover along with the rigid/flexible strip electrodes and clasping studs/holes.
Figure 3B:
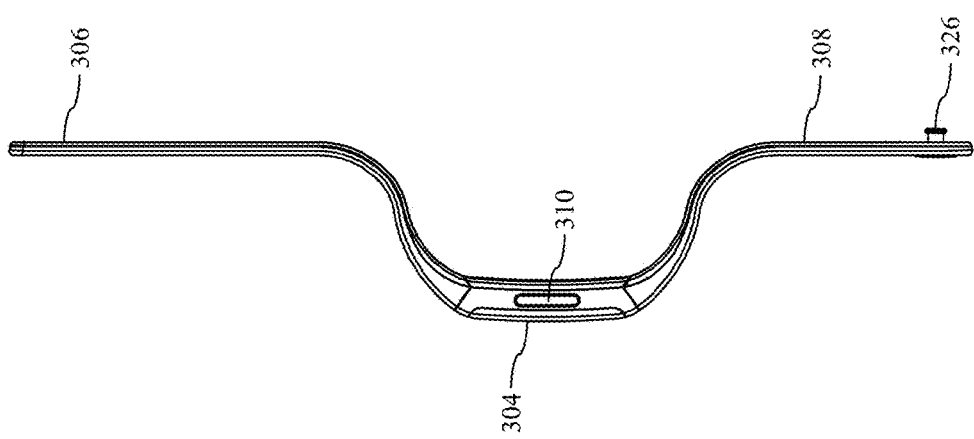
Figure 3A:
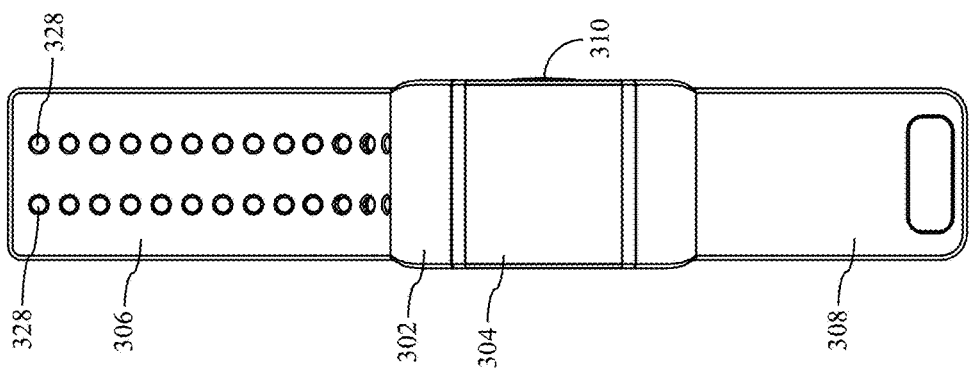

FIGS. 3A-3C illustrate one embodiment of the front, side, and back of the secondary smart band showing the front cover along with the rigid/flexible strip electrodes and clasping studs/holes. The design, footprint, materials, dimensions, weight, and fabrication of the secondary smart band is similar to that of the primary smart band. The only difference is that the secondary smart band does not have a display. In this example, the secondary smart band comprises an enclosure 302 made of stainless steel, a plastic front cover 304, upper 306 and lower 308 straps made of flexible rubber, and an on/off button 310. It also comprises three rigid strip electrodes 312, 314, 316 embedded in a plastic backplate 318 and three flexible strip electrodes 320, 322, 324 embedded in the upper 306 and lower 308 straps. Studs 326 made of hard rubber and holes 328 are provided on the secondary smart band straps for clasping it snugly around the wrist. It will be appreciated that while two sets of studs 212 and holes 214 are shown, a single set, multiple sets or other arrangements could be used instead.

There are several advantages of the disclosed rigid and flexible strip electrodes over isolated and/or small footprint electrodes proposed in prior art. First, the surface area of each electrode is maximized to improve overall connectivity around the wrist. Second, since each electrode touches the skin all around the wrist, its reliability of coming in contact with the skin at all times (for example, during sleep) is significantly higher. Finally, by forming a connection all around the wrist, the dependence of each electrode's performance on its physical position around the wrist is minimized. Therefore, the smart band pair described in this invention, by virtue of its rigid and flexible strip electrodes, is able to acquire good quality ECG data with a high degree of accuracy.

Figure 4:
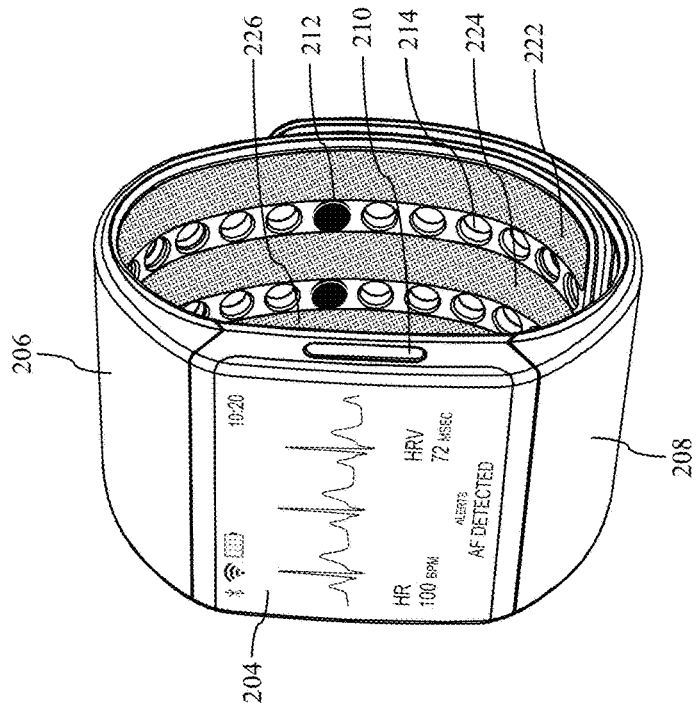
FIG. 4 illustrates an alternate view of the primary smart band showing the touchscreen display along with the straps, clasping mechanism, and flexible strip electrodes.

FIG. 4 illustrates an alternate view of the primary smart band showing the touchscreen display along with the straps, clasping mechanism, and flexible strip electrodes. The profile shape of the primary smart band straps 206, 208 is curved, and they provide a snug fit around the wrist using the stud 212 and hole 214 clasping mechanism. When worn around the wrist, the rigid strip electrodes (not shown) and the flexible strip electrodes 222, 224, 226 embedded in the straps 206, 208 make contact with the skin all around the wrist. The primary smart band is switched on by activating the on/off button 210. The touchscreen display 204 helps in visualizing ECG data and its analysis in real-time. In one example, the touchscreen 204 displays real-time ECG waveform data along with HR/HRV metrics and pertinent alarms when these metrics are out of range. In another example, the user can interact with the touchscreen display 204 to perform tasks like reviewing historic ECG data and/or sending a distress signal to other connected users/devices.

Figure 5:
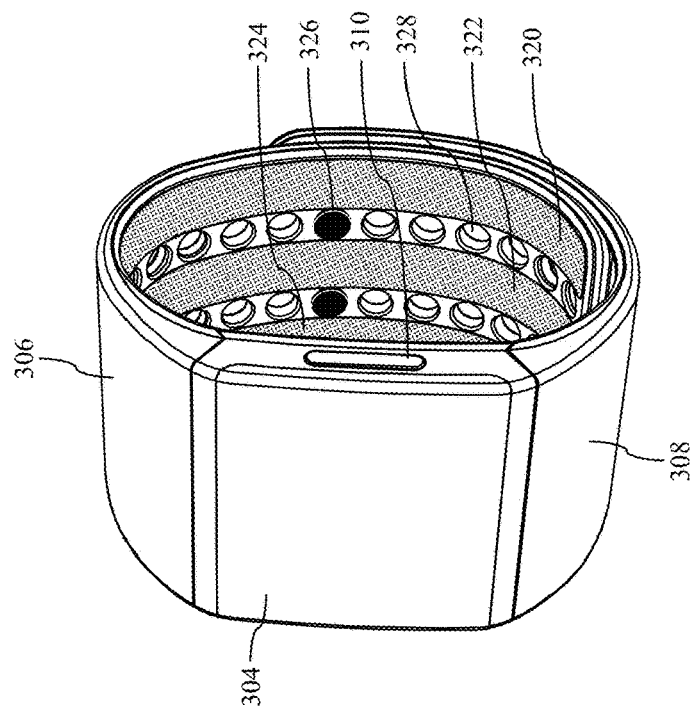
FIG. 5 illustrates an alternate view of the secondary smart band showing the front cover along with the straps, clasping mechanism, and flexible strip electrodes.

FIG. 5 illustrates an alternate view of the secondary smart band showing the front cover along with the straps, clasping mechanism, and flexible strip electrodes. The profile shape of the secondary smart band straps 306, 308 is curved, and they provide a snug fit around the wrist using the stud 326 and hole 328 clasping mechanism. When worn around the wrist, the rigid strip electrodes (not shown) and the flexible strip electrodes 320, 322, 324 embedded in the straps 306, 308 make contact with the skin all around the wrist. The secondary smart band is switched on by activating the on/off button 310. In place of a touchscreen display, in this embodiment the secondary smart band is provided with a plastic front cover 304.

Figure 6:
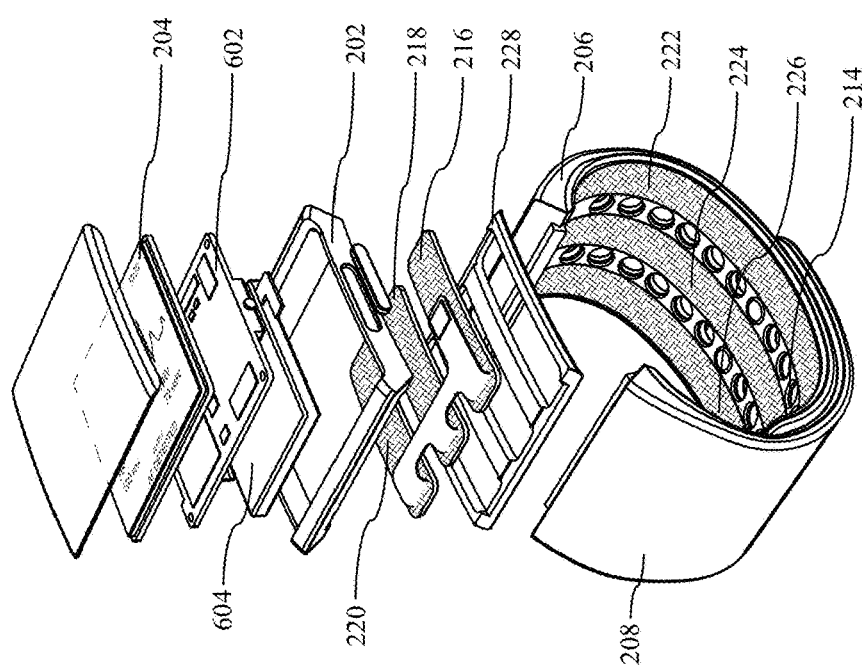
FIG. 6 illustrates an exploded view of the primary smart band showing the key components.

FIG. 6 illustrates an exploded view of the primary smart band showing the key components in one embodiment. These include a touchscreen display 204, printed circuit board 602 containing all related hardware and running the desired software, enclosure 202, rechargeable battery 604, backplate 228 with embedded rigid strip electrodes 216, 218, 220 and straps 206, 208 with flexible strip electrodes 222, 224, 226 and clasping holes 214.

Figure 7:
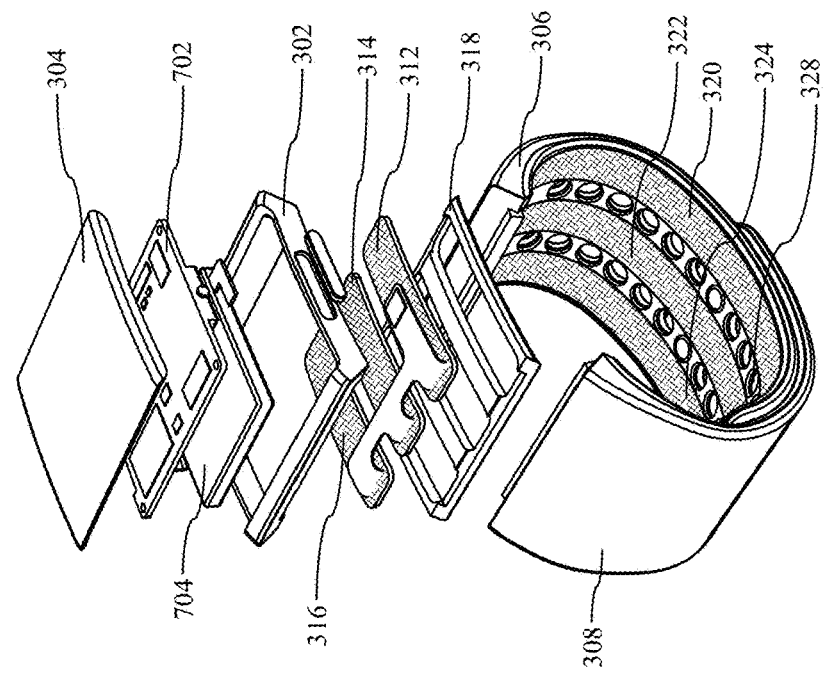
FIG. 7 illustrates an exploded view of the secondary smart band showing the key components.

FIG. 7 illustrates an exploded view of the secondary smart band showing the key components in one embodiment. These include a plastic front cover 304, printed circuit board 702 containing all related hardware and running the desired software, enclosure 302, rechargeable battery 704, backplate 318 with embedded rigid strip electrodes 312, 314, 316 and straps 306, 308 with flexible strip electrodes 320, 322, 324 and clasping holes 328.

In one example, desired components of the primary (FIG. 6) and secondary (FIG. 7) smart bands are provided with clipping mechanisms enabling them to be snap fitted.

Figure 8:
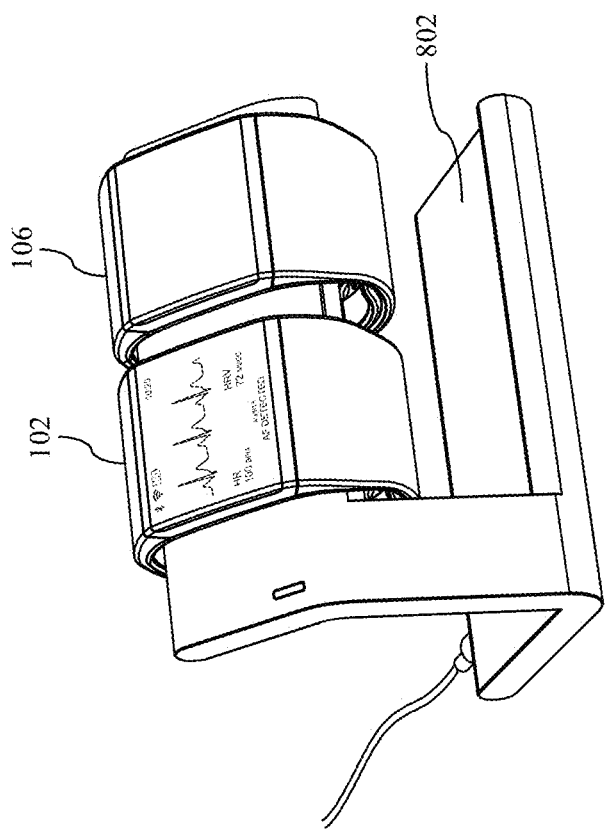
FIG. 8 illustrates the smart band pair being charged on a twin wireless charging unit.

FIG. 8 illustrates the smart band pair being charged on a twin wireless charging unit. Both primary 102 and secondary 106 smart bands are provided with rechargeable batteries 604, 704 and wireless charging hardware/software. The smart band pair 102, 106 can therefore be charged on a twin wireless charging unit 802. It will be appreciated that other charging arrangements, including wired, could also be used.

Figure 9:
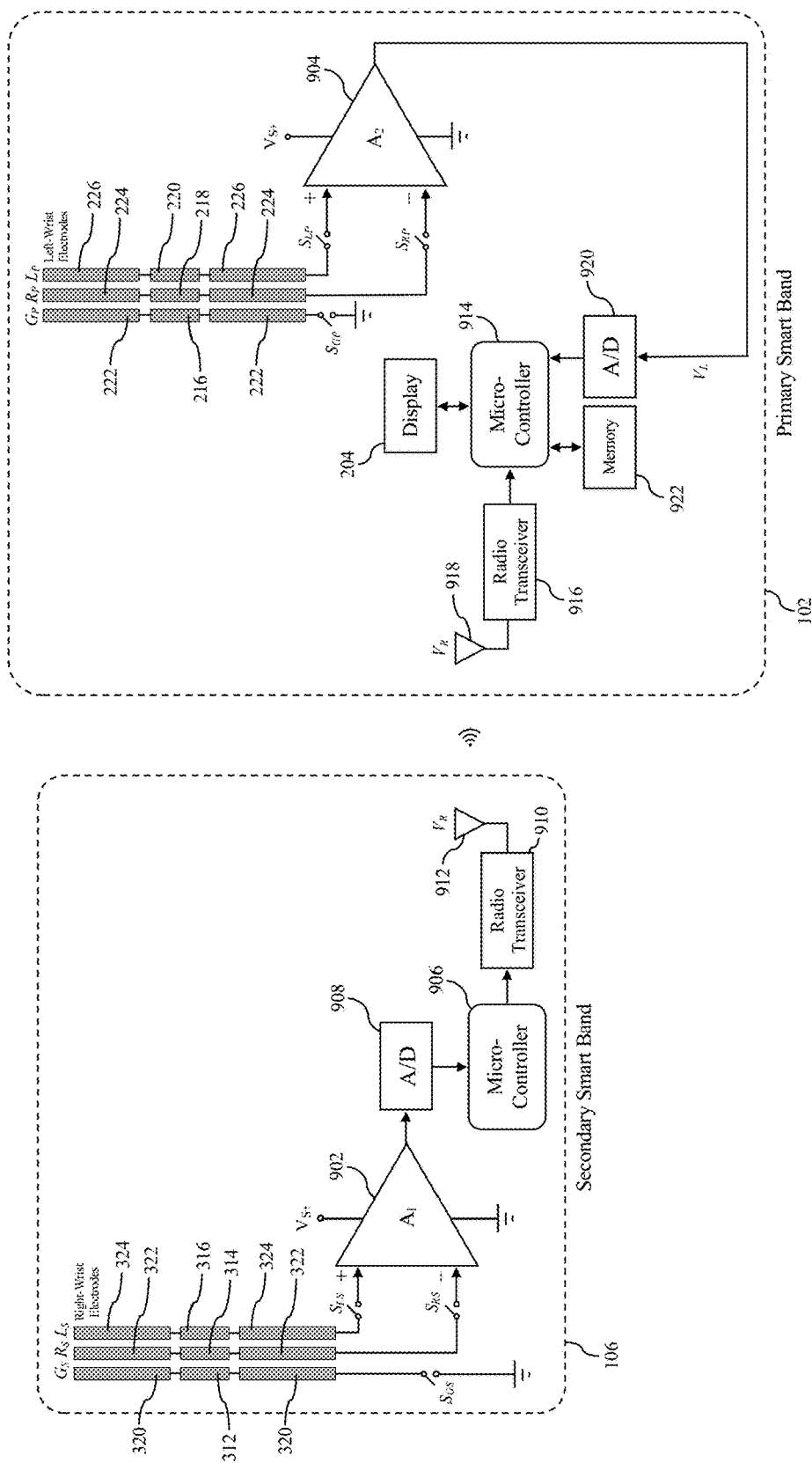
FIG. 9 illustrates an operational diagram of the smart band pair whereby one electrode in each is a ground and biopotential data from both smart bands is sent directly to the microcontroller for processing.

FIG. 9 illustrates an example operational diagram of the smart band pair whereby one electrode in each is a ground and biopotential data from both smart bands is sent directly to the microcontroller for processing. In this example, the secondary smart band 106 is attached to a user's right wrist and the primary smart band 102 is attached to the user's left wrist.

In FIG. 9, in the secondary smart band 106, the three rigid strip electrodes 312, 314, 316 and the three flexible strip electrodes 320, 322, 324 are electrically connected. Similarly, in the primary smart band 102, the three rigid strip electrodes 216, 218, 220 and the three flexible strip electrodes 222, 224, 226 are electrically connected.

Referring to FIG. 9, the secondary smart band 106 comprises three strip electrodes namely ground 312, 320, right 314, 322, and left 316, 324 electrodes that are connected to biopotential amplification and conditioning circuitry 902 via three digital switches $S_{GS}$, $S_{RS}$, $S_{LS}$. Similarly, the primary smart band 102 comprises three strip electrodes namely ground 216, 222, right 218, 224, and left 220, 226 electrodes that are connected to biopotential amplification and conditioning circuitry 904 via three digital switches $S_{GP}$, $S_{RP}$, $S_{LP}$.

As shown in FIG. 9, the right-side biopotential signal ($V_R$) measured by the secondary smart band ground 312, 320, right 314, 322, and left 316, 324 electrodes is acquired by the microcontroller 906 via an analog-to-digital (A/D) converter 908. Using the radio transceiver 910 and antenna 912, the microcontroller 906 wirelessly sends the right-side biopotential signal ($V_R$) to the primary smart band 102 attached to the user's left wrist. The primary smart band microcontroller 914 wirelessly receives the right-side biopotential signal ($V_R$) via its radio transceiver 916 and antenna 918. At the same time, the left-side biopotential signal ($V_L$) measured by the primary smart band ground 216, 222, right 218, 224, and left 220, 226 electrodes is also acquired by the primary smart band microcontroller 914 via an A/D converter 920. The primary smart band microcontroller 914 then processes and combines the biopotential signals $V_R$ and $V_L$ to produce a high-fidelity ECG signal. In its simplest form, a single-lead ECG signal ($V_I$) is synthesized by the smart band microcontroller 914 as per equation 1:

$$V_I = V_L - V_R \tag{1}$$

In FIG. 9, the acquired ECG signal $V_I$ and related analytics are stored inside memory 922 and all related information is displayed in real-time on the touchscreen display 204 of the primary smart band 102. Moreover, the primary smart band 102 also wirelessly transmits all ECG-related information via its radio transceiver 916 and antenna 918 to external devices 110 like smartphones, PCs, and tablets.

Figure 10:
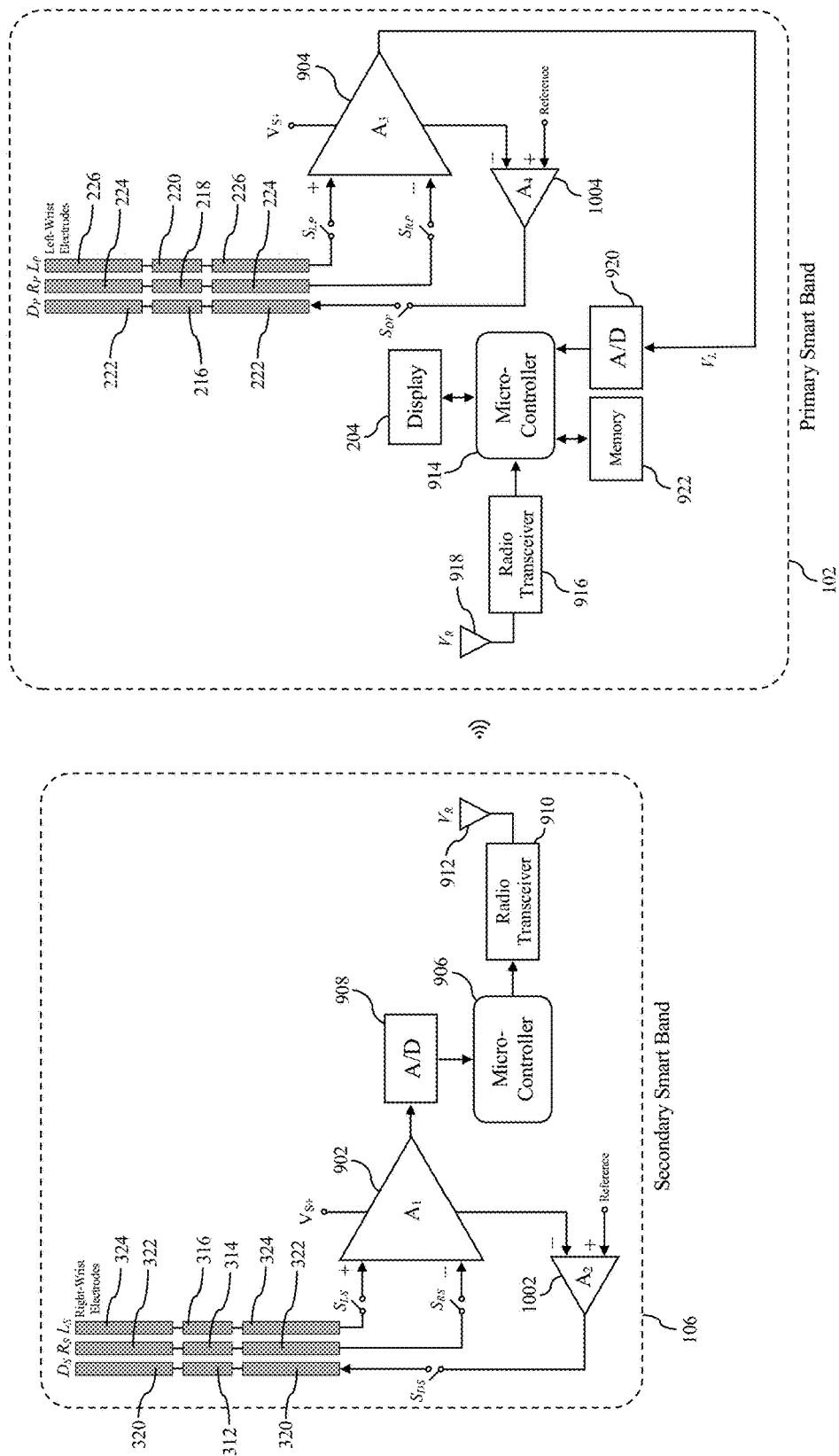
FIG. 10 illustrates an operational diagram of the smart band pair whereby one electrode in each is an RLD and biopotential data from both smart bands is sent directly to the microcontroller for processing.

FIG. 10 illustrates an example operational diagram of the smart band pair whereby one electrode in each is an RLD and biopotential data from both smart bands is sent directly to the microcontroller for processing. In this example, the secondary smart band 106 is attached to user's right wrist and the primary smart band 102 is attached to user's left wrist.

In FIG. 10, the secondary smart band strip electrodes 312, 320, 314, 322, 316, 324 and the primary smart band strip electrodes 216, 222, 218, 224, 220, 226 are connected in a manner similar to that described for FIG. 9.

As shown in FIG. 10, the secondary smart band 106 comprises three strip electrodes namely RLD 312, 320, right 314, 322, and left 316, 324 electrodes that are connected to biopotential amplification/conditioning circuitry 902 and RLD circuitry 1002 via three digital switches $S_{DS}$, $S_{RS}$, $S_{LS}$. Similarly, the primary smart band 102 comprises three strip electrodes namely RLD 216, 222, right 218, 224, and left 220, 226 electrodes that are connected to biopotential amplification/conditioning circuitry 904 and RLD circuitry 1004 via three digital switches $S_{DP}$, $S_{RP}$, $S_{LP}$.

Referring to FIG. 10, the method for single-lead ECG data acquisition is similar to that described for FIG. 9. The only difference is that the quality and fidelity of the acquired ECG signal is further augmented by virtue of the RLD electrodes 312, 320, 216, 222 and circuitry 1002, 1004 that minimize common mode noise.

Figure 11:
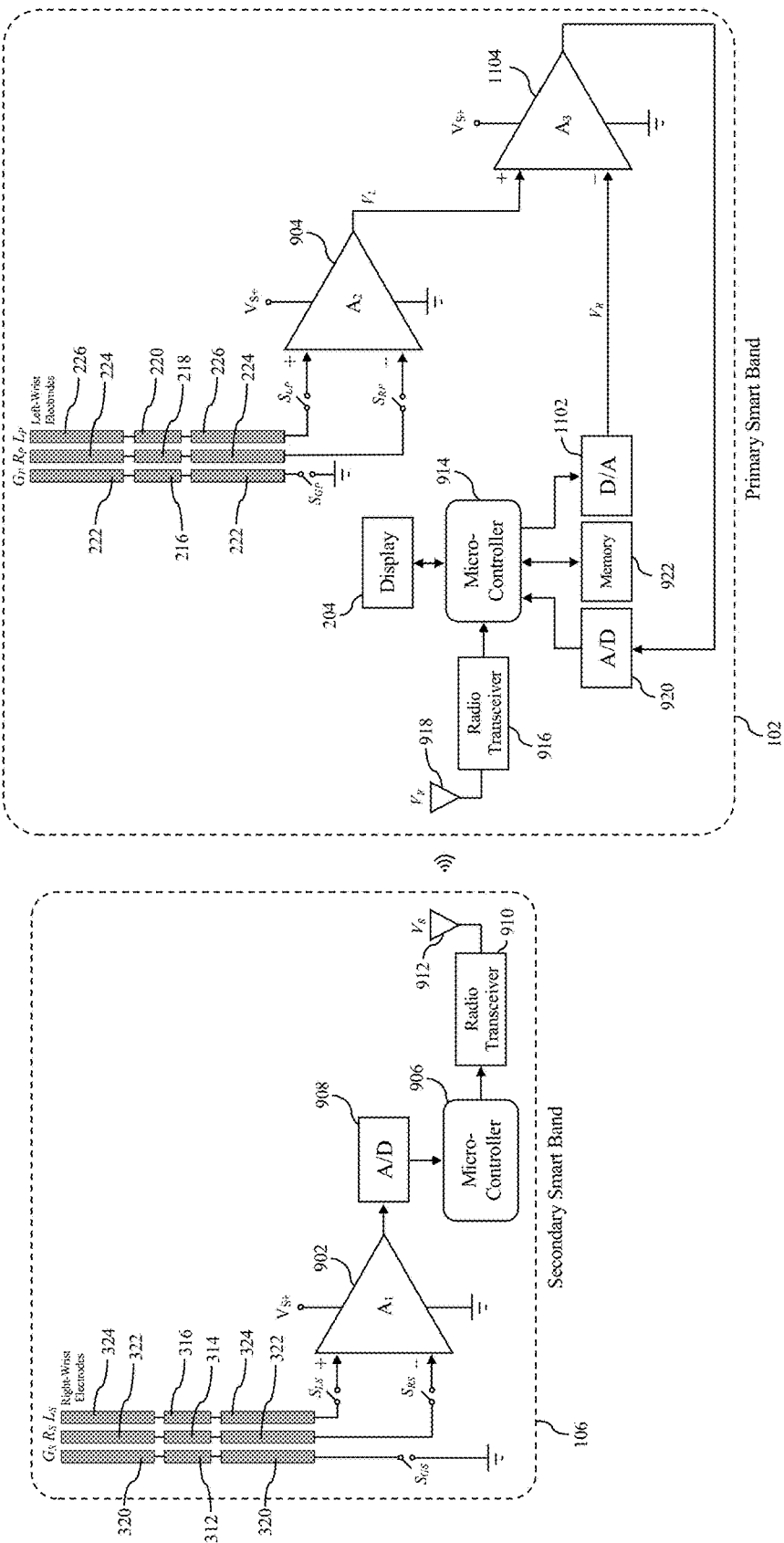
FIG. 11 illustrates an operational diagram of the smart band pair whereby one electrode in each is a ground and biopotential data from both smart bands is first sent to a differential amplifier and then to the microcontroller for processing.

FIG. 11 illustrates an example operational diagram of the smart band pair whereby one electrode in each is a ground and biopotential data from both smart bands is first sent to a differential amplifier and then to the microcontroller for processing. In this example, the secondary smart band 106 is attached to user's right wrist and the primary smart band 102 is attached to user's left wrist.

In FIG. 11, the secondary smart band strip electrodes 312, 320, 314, 322, 316, 324 and the primary smart band strip electrodes 216, 222, 218, 224, 220, 226 are connected in a manner similar to that described for FIG. 9.

As shown in FIG. 11, the secondary smart band 106 comprises three strip electrodes namely ground 312, 320, right 314, 322, and left 316, 324 electrodes that are connected to biopotential amplification and conditioning circuitry 902 via three digital switches $S_{GS}$, $S_{RS}$, $S_{LS}$. Similarly, the primary smart band 102 comprises three strip electrodes namely ground 216, 222, right 218, 224, and left 220, 226 electrodes that are connected to biopotential amplification and conditioning circuitry 904 via three digital switches $S_{GP}$, $S_{RP}$, $S_{LP}$.

Referring to FIG. 11, similar to the method described for FIG. 9, the primary smart band microcontroller 914 wirelessly receives the right-side biopotential signal ($V_R$) via its radio transceiver 916 and antenna 918. The microcontroller 914 then sends this signal via a digital-to-analog (D/A) converter 1102 to a differential amplifier 1104. At the same time, this differential amplifier 1104 also receives the left-side biopotential signal ($V_L$) measured by the primary smart band strip electrodes 216, 222, 218, 224, 220, 226 in conjunction with the biopotential amplification and conditioning circuitry 904. The primary smart band microcontroller 914 then acquires the amplified ECG signal output from the differential amplifier 1104 via the A/D converter 920. This highlights another method for amplifying the biopotential signals $V_R$ and $V_L$, for obtaining a high-quality ECG signal.

Figure 12:
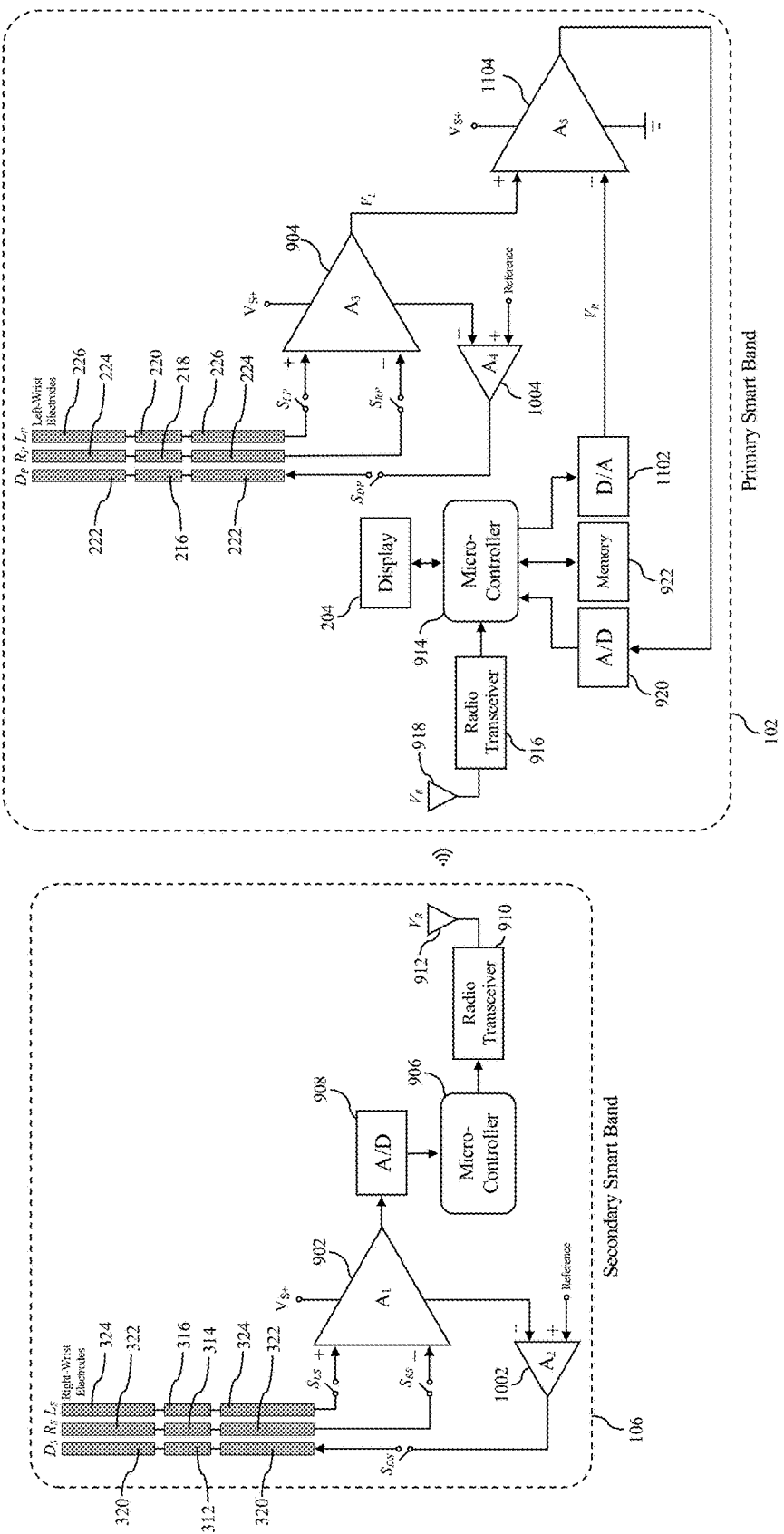
FIG. 12 illustrates an operational diagram of the smart band pair whereby one electrode in each is an RLD and biopotential data from both smart bands is first sent to a differential amplifier and then to the microcontroller for processing.

FIG. 12 illustrates an example operational diagram of the smart band pair whereby one electrode in each is an RLD and biopotential data from both smart bands is first sent to a differential amplifier and then to the microcontroller for processing. In this example, the secondary smart band 106 is attached to user's right wrist and the primary smart band 102 is attached to user's left wrist.

In FIG. 12, the secondary smart band strip electrodes 312, 320, 314, 322, 316, 324 and the primary smart band strip electrodes 216, 222, 218, 224, 220, 226 are connected in a manner similar to that described for FIG. 9.

As shown in FIG. 12, the secondary smart band 106 comprises three strip electrodes namely RLD 312, 320, right 314, 322, and left 316, 324 electrodes that are connected to biopotential amplification/conditioning circuitry 902 and RLD circuitry 1002 via three digital switches $S_{DS}$, $S_{RS}$, $S_{LS}$. Similarly, the primary smart band 102 comprises three strip electrodes namely RLD 216, 222, right 218, 224, and left 220, 226 electrodes that are connected to biopotential amplification/conditioning circuitry 904 and RLD circuitry 1004 via three digital switches $S_{DP}$, $S_{RP}$, $S_{LP}$.

Referring to FIG. 12, the method for single-lead ECG data acquisition is similar to that described for FIG. 11. The only difference is that the quality and fidelity of the acquired ECG signal is further augmented by virtue of the RLD electrodes 312, 320, 216, 222 and circuitry 1002, 1004 that minimize common mode noise.

Figure 13:
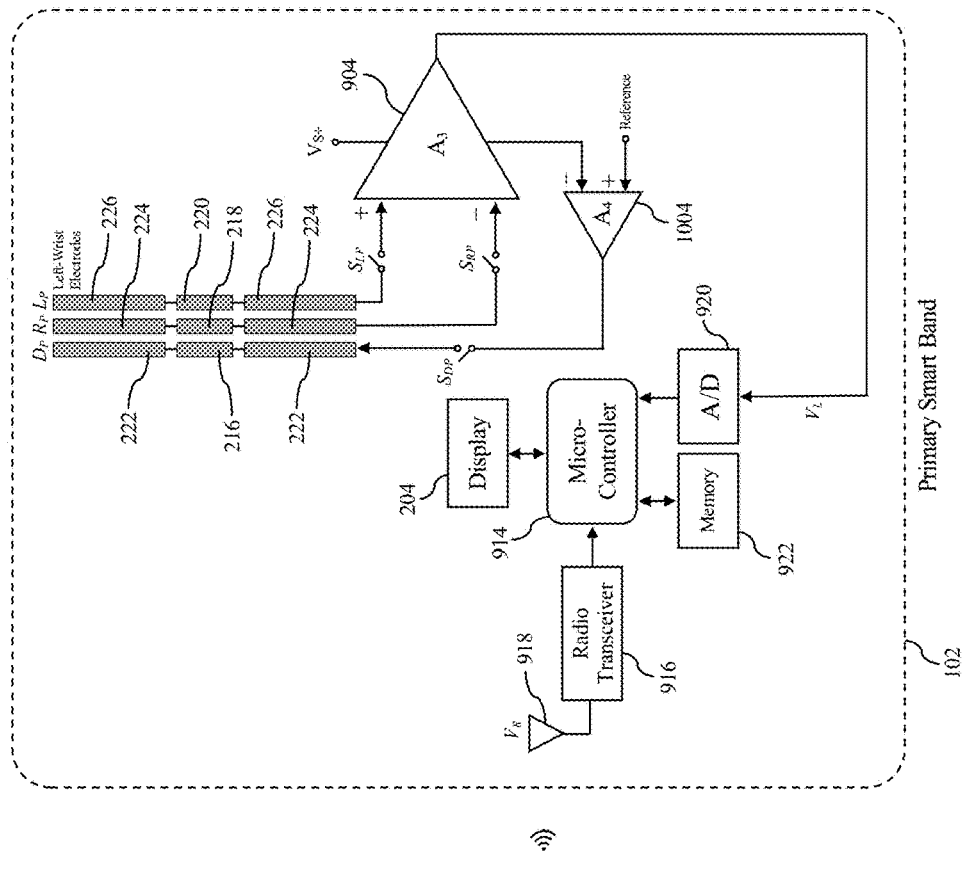
FIG. 13 illustrates an operational diagram of the smart band pair whereby one electrode in the secondary is a ground while one electrode in the primary is an RLD and biopotential data from both smart bands is sent directly to the microcontroller for processing.
Figure 13:
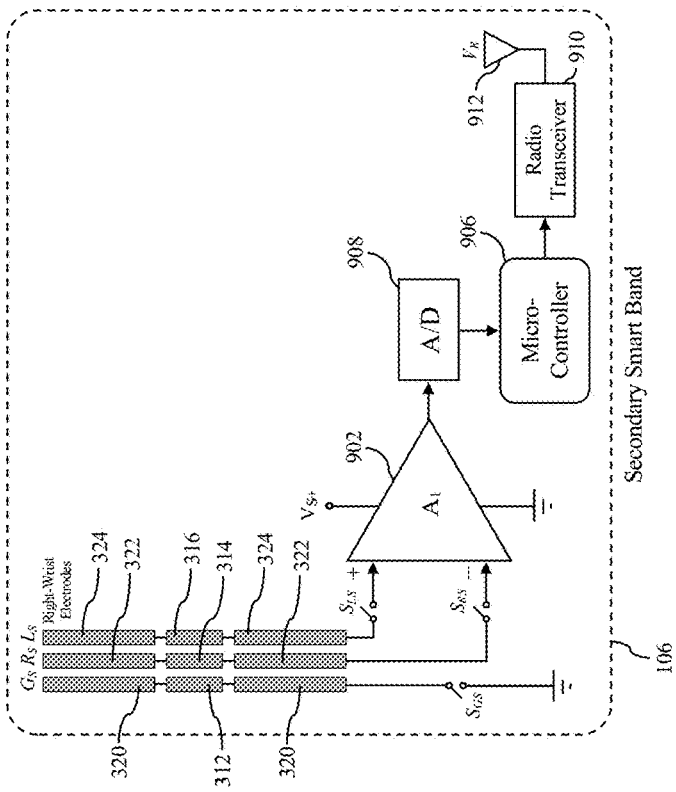

FIG. 13 illustrates an example operational diagram of the smart band pair whereby one electrode in the secondary is a ground while one electrode in the primary is an RLD and biopotential data from both smart bands is sent directly to the microcontroller for processing. In this example, the secondary smart band 106 is attached to user's right wrist and the primary smart band 102 is attached to user's left wrist.

In FIG. 13, the secondary smart band strip electrodes 312, 320, 314, 322, 316, 324 and the primary smart band strip electrodes 216, 222, 218, 224, 220, 226 are connected in a manner similar to that described for FIG. 9.

As shown in FIG. 13, the secondary smart band 106 comprises three strip electrodes namely ground 312, 320, right 314, 322, and left 316, 324 electrodes that are connected to biopotential amplification/conditioning circuitry 902 via three digital switches $S_{GS}$, $S_{RS}$, $S_{LS}$. On the other hand, the primary smart band 102 comprises three strip electrodes namely RLD 216, 222, right 218, 224, and left 220, 226 electrodes that are connected to biopotential amplification/conditioning circuitry 904 and RLD circuitry 1004 via three digital switches $S_{DP}$, $S_{RP}$, $S_{LP}$.

Referring to FIG. 13, the method for single-lead ECG data acquisition is similar to that described for FIG. 9. The only difference is that the secondary smart band 106 comprises a ground electrode 312, 320 while the primary smart band 102 comprises an RLD electrode 216, 222 to further reduce noise and enhance quality and fidelity of the acquired ECG signal.

Figure 14:
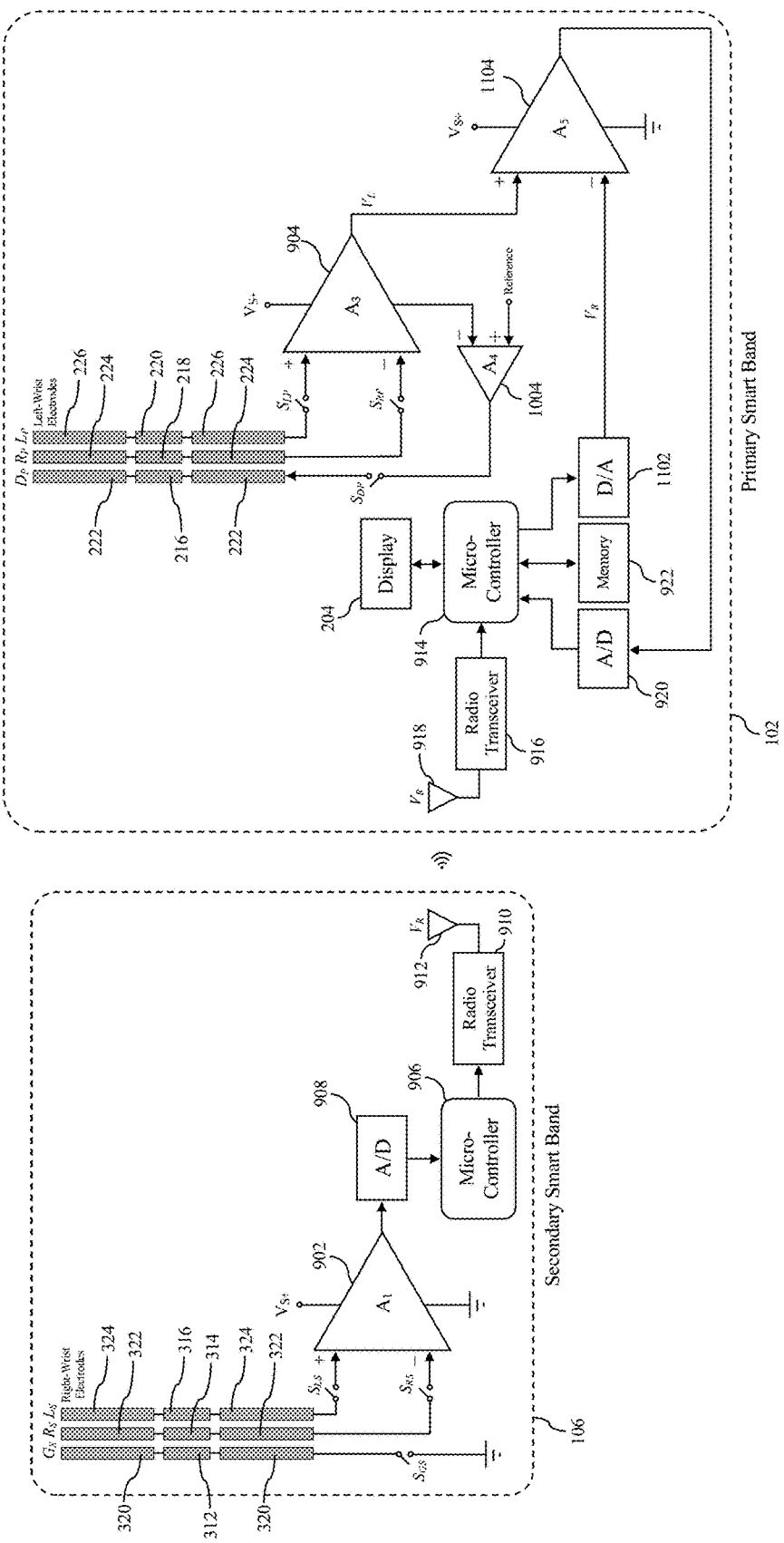
FIG. 14 illustrates an operational diagram of the smart band pair whereby one electrode in the secondary is a ground while one electrode in the primary is an RLD and biopotential data from both smart bands is first sent to a differential amplifier and then to the microcontroller for processing.

FIG. 14 illustrates an example operational diagram of the smart band pair whereby one electrode in the secondary is a ground while one electrode in the primary is an RLD and biopotential data from both smart bands is first sent to a differential amplifier and then to the microcontroller for processing. In this example, the secondary smart band 106 is attached to user's right wrist and the primary smart band 102 is attached to user's left wrist.

In FIG. 14, the secondary smart band strip electrodes 312, 320, 314, 322, 316, 324 and the primary smart band strip electrodes 216, 222, 218, 224, 220, 226 are connected in a manner similar to that described for FIG. 9.

As shown in FIG. 14, the secondary smart band 106 comprises three strip electrodes namely ground 312, 320, right 314, 322, and left 316, 324 electrodes that are connected to biopotential amplification/conditioning circuitry 902 via three digital switches $S_{GS}$, $S_{RS}$, $S_{LS}$. On the other hand, the primary smart band 102 comprises three strip electrodes namely RLD 216, 222, right 218, 224, and left 220, 226 electrodes that are connected to biopotential amplification/conditioning circuitry 904 and RLD circuitry 1004 via three digital switches $S_{DP}$, $S_{RP}$, $S_{LP}$.

Referring to FIG. 14, the method for single-lead ECG data acquisition is similar to that described for FIG. 11. The only difference is that the secondary smart band 106 comprises a ground electrode 312, 320 while the primary smart band 102 comprises an RLD electrode 216, 222 to further reduce noise and enhance quality and fidelity of the acquired ECG signal.

In the examples shown in FIGS. 9-14, switches $S_{GP}/S_{DP}$, $S_{RP}$, $S_{LP}$ are provided for primary smart band strip electrodes 216, 222, 218, 224, 220, 226 and switches $S_{GS}/S_{DS}$, $S_{RS}$, $S_{LS}$ are provided for secondary smart band strip electrodes 312, 320, 314, 322, 316, 324. This allows for different electrode configurations and connections to be used for each smart band to minimize signal-to-noise ratio (SNR), thus further enhancing ECG signal quality. This feature is useful for device testing and calibration whereby related hardware/software can be fine-tuned to obtain optimum signal quality.

A truth table in Table 1 below summarizes all possible electrode configurations and connections that can be used on each smart band to optimize and augment ECG signal quality. In Table 1, $S_G$ is the ground electrode switch, $S_D$ is the RLD electrode switch, $S_L$ is the left electrode switch, and $S_R$ is the right electrode switch of the primary and/or secondary smart band. The on state of an electrode switch is represented by true (T) while the off state of an electrode switch is represented by false (F).

| $S_G/S_D$ | $S_L$ | $S_R$ |
|---|---|---|
| T | F | F |
| F | T | F |
| F | F | T |
| T | T | F |
| T | F | T |
| F | T | T |
| T | T | T |
| F | F | F |

Figure 15:
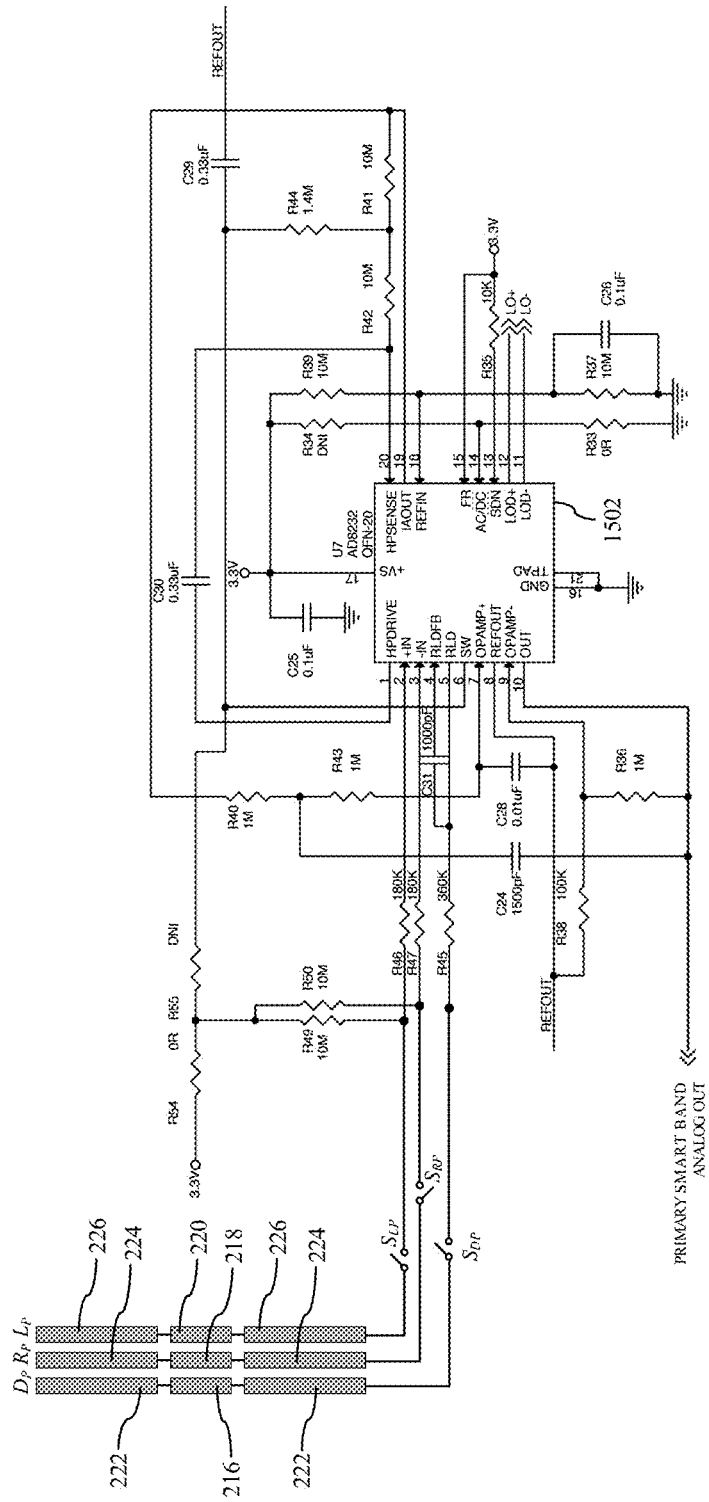
FIG. 15 illustrates the circuit diagram of a biopotential amplifier with an RLD strip electrode implemented using Analog Devices AD8232 chip.

FIG. 15 illustrates an example circuit diagram of a biopotential amplifier with an RLD strip electrode implemented using Analog Devices AD8232 chip. The biopotential amplifiers described in FIG. 9-14, can be easily implemented using commercially available ECG analog front ends like the AD8232 chip 1502. The disclosed circuit diagram shows the values of various electronic components and the primary smart band strip electrodes 216, 222, 218, 224, 220, 226 connected to the AD8232 chip 1502. In this case, the primary smart band strip electrodes 216, 222 are RLD electrodes since they are connected to an RLD circuitry inside the AD8232 chip 1502.

Figure 16:
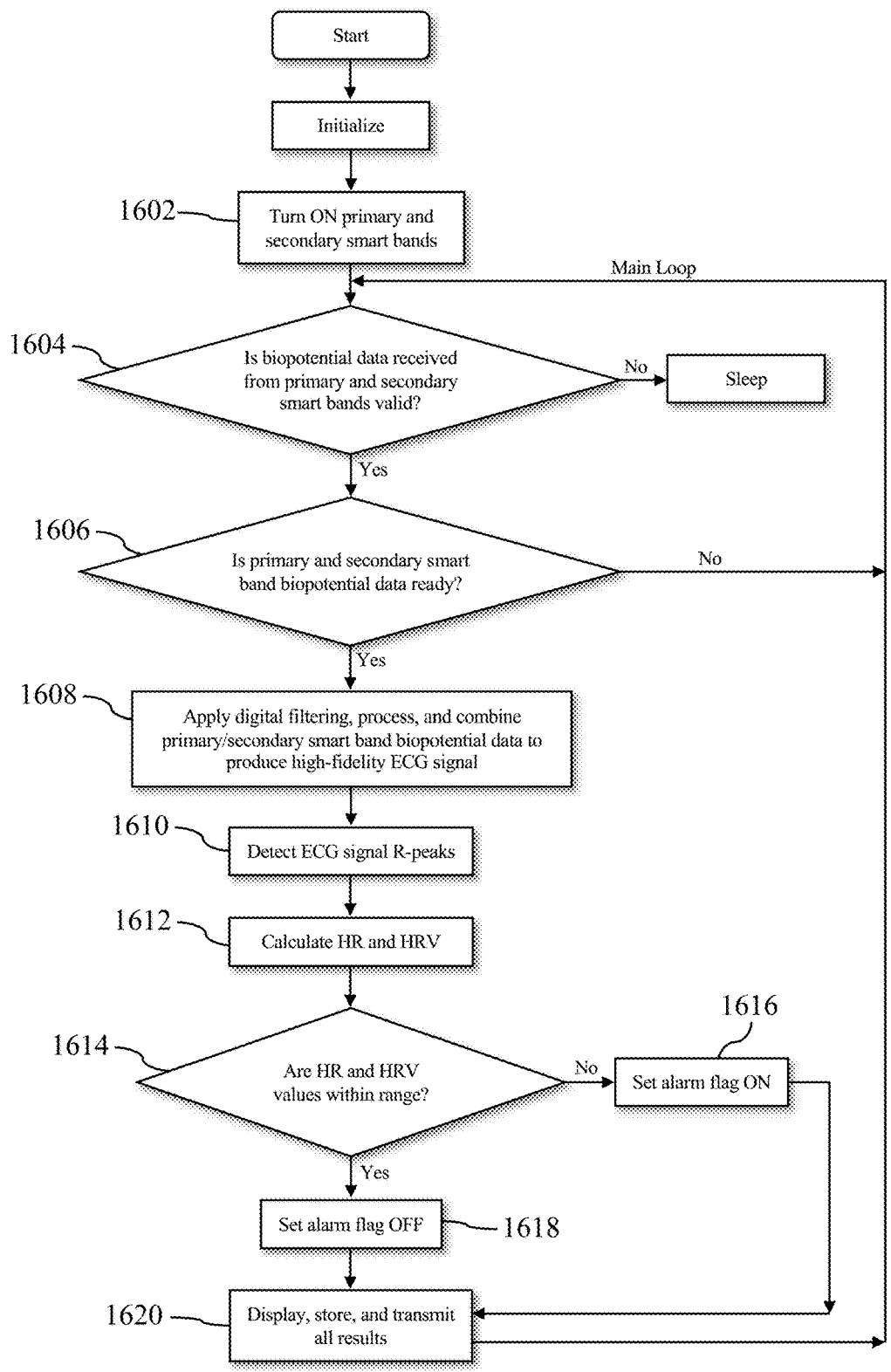
FIG. 16 illustrates a flowchart depicting the method of continuous ECG monitoring and HR/HRV analysis whereby biopotential data from both smart bands is sent directly to the microcontroller for processing.

FIG. 16 illustrates a flowchart depicting one example method of continuous ECG monitoring and HR/HRV analysis whereby biopotential data from both smart bands is sent directly to the microcontroller for processing. At step 1602 both primary 102 and secondary 106 smart bands are switched on using buttons 210 and 310. At step 1604 the microcontroller 914 inside the primary smart band checks whether biopotential data that is wirelessly received from the secondary smart band 106 and the biopotential data that is received via A/D converter of the primary smart band 102 is valid. If the data in step 1604 is found to be valid, the primary smart band 102 waits for this data to be ready for processing at step 1606. Once all biopotential data is ready, the primary smart band microcontroller 914 performs various analyses like digital filtering and other mathematical operations on this data at step 1608 to produce high-fidelity ECG data. At step 1610, the primary smart band microcontroller 914 detects ECG R-peaks and then at step 1612 it computes metrics like HR and HRV. In this example, at step 1614, the primary smart band microcontroller 914 checks the calculated HR/HRV metrics against predefined acceptable values. Based on whether the calculated HR/HRV parameters are in range or out of range, alarm flags are accordingly set at steps 1616 and 1618. At step 1620, the primary smart band touchscreen display 204 shows ECG data and related analytics along with the alarm status in real-time. Moreover, at step 1620, the primary smart band wirelessly transmits all ECG data and related analytics to third-party devices 110.

Figure 17:
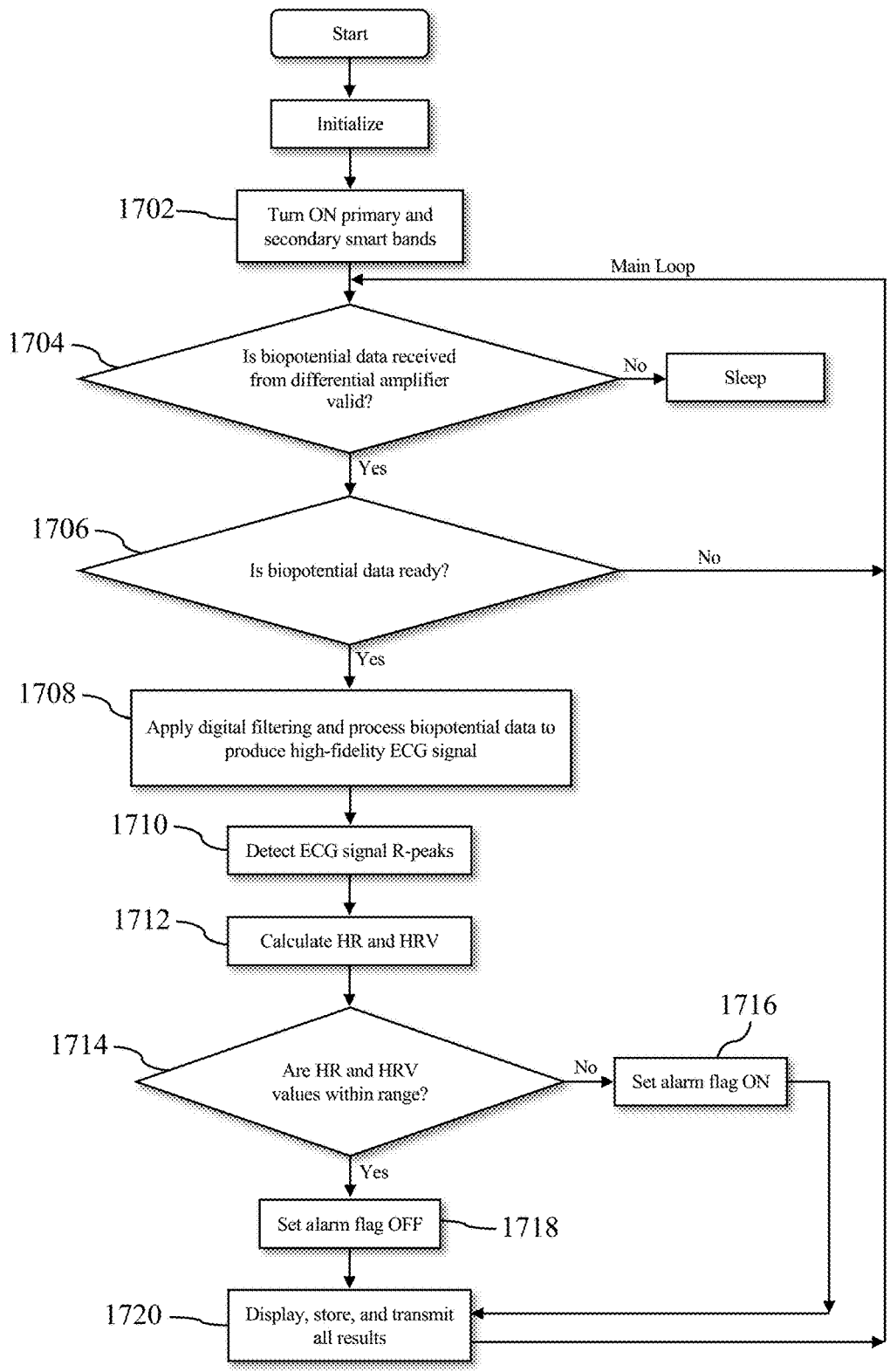
FIG. 17 illustrates a flowchart depicting the method of continuous ECG monitoring and HR/HRV analysis whereby biopotential data from both smart bands is first sent to a differential amplifier and then to the microcontroller for processing.

FIG. 17 illustrates an example flowchart depicting the method of continuous ECG monitoring and HR/HRV analysis whereby biopotential data from both smart bands is first sent to a differential amplifier and then to the microcontroller for processing. This flowchart describes a method for ECG data acquisition and analysis that is similar to that described for FIG. 16. The main difference is that at step 1704 the primary smart band microcontroller 914 checks for the validity of the amplified primary and secondary smart band biopotential data that it receives from the differential amplifier 1104 inside the primary smart band 102.

Figure 18:
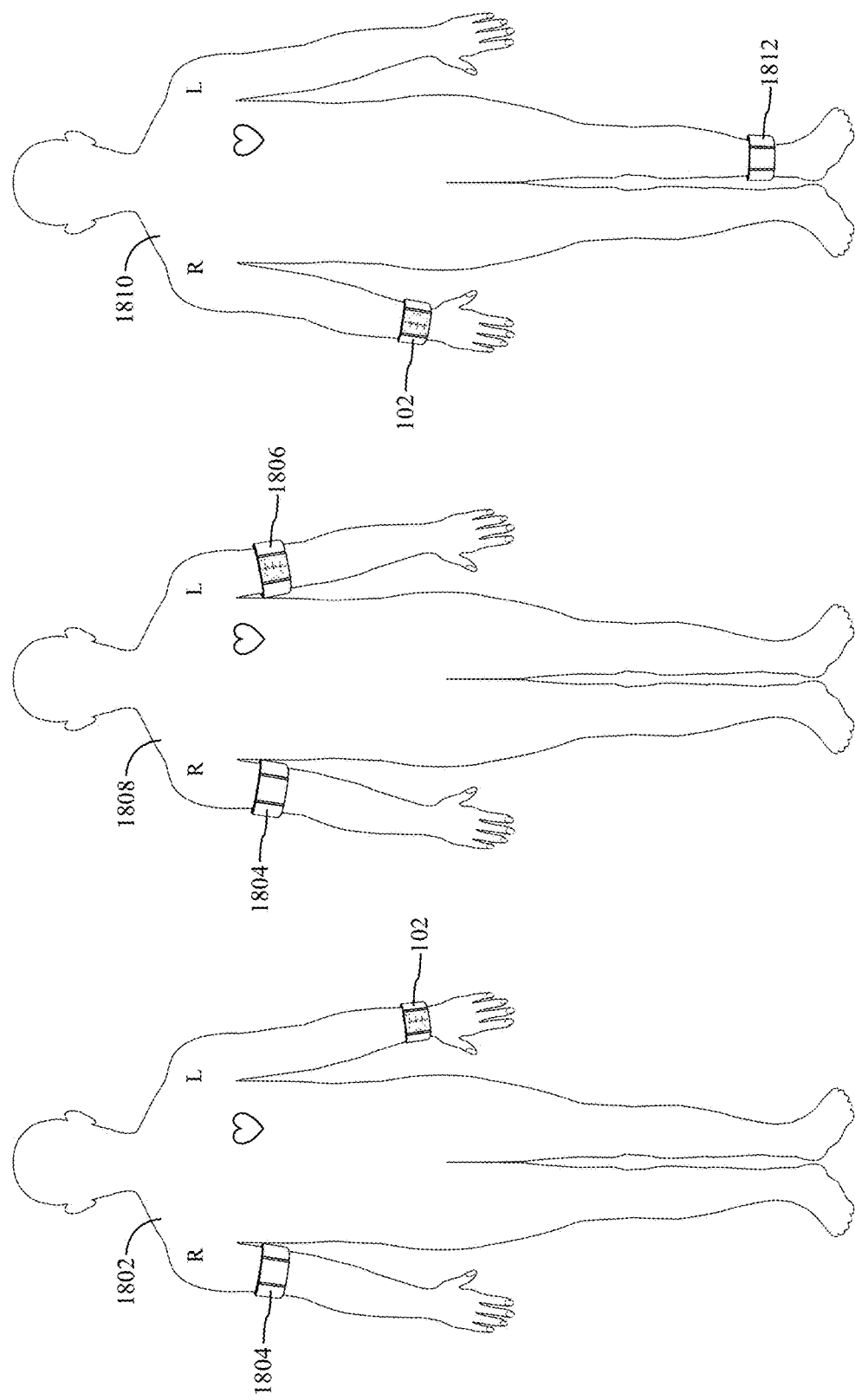
FIG. 18 illustrates examples of various locations on the human body where wearables employing the underlying design and principle of the current invention can be attached to undertake continuous leadless ECG monitoring.

FIG. 18 illustrates examples of various locations on the human body where wearables employing the underlying design and principle of the current invention can be attached to undertake continuous leadless ECG monitoring. As illustrated at 1802, the primary smart band 102 can be worn around the left wrist while a secondary smart band 1804 can be worn around the right upper arm. As illustrated at 1808, a primary smart band 1806 can be worn around the left upper arm while the secondary smart band 1804 can be worn around the right upper arm. Finally, as illustrated at 1810, the primary smart band 102 can be worn around the right wrist while a secondary smart band 1812 can be worn around the left ankle. These examples demonstrate that the disclosed wireless smart band pair and/or other similar wearable pair can be attached at various locations along the four limbs to accomplish leadless Einthoven-type single-lead ECG measurements.

It will be appreciated by one skilled in the art that variants can exist in the above-described arrangements and applications.

For example, in one embodiment, the described smart band pair can also be used for intermittent ECG monitoring and analysis. For example, the user can operate the on/off switches 210, 310 on the primary and secondary smart bands 102, 106 to enable and disable ECG data acquisition and analysis as required. In another example, the microcontrollers 906, 914, inside the primary and secondary smart bands 102, 106 can be programmed to acquire and analyze ECG data at predefined intervals, for example, acquire and analyze ECG data for 5 minutes every 30 minutes.

In another embodiment, the described smart band pair can be used solely for biopotential data acquisition and transmission while all data processing/analysis can be done on external devices. For example, the primary smart band 102 can acquire and wirelessly transmit the first biopotential data to a smartphone and the secondary smart band 106 can acquire and wirelessly transmit the second biopotential data to the same smartphone. This smartphone can then process and combine the received first and second biopotential data to produce a high-fidelity ECG signal. The smartphone can also perform further analyses on the ECG signal like R-peak detection, HR/HRV evaluation, and alarm generation. It will be obvious to those skilled in the art that the said smartphone can be replaced by a laptop, tablet, and/or any similar computing device.

The specific examples provided herein relate to a continuous leadless electrocardiogram monitor, however, the materials, methods of application and arrangements of the invention can be varied. The scope of the claims should not be limited by the preferred embodiments set forth in the examples but should be given the broadest interpretation consistent with the description as a whole.

What is claimed is:

1. An electrocardiogram monitor comprising:
   a primary smart band having at least three electrodes configured to be either RLD-left-right or ground-left-right electrodes that are configured to contact skin of a user and measure a first high-fidelity biopotential signal; and
   a secondary smart band having at least three electrodes configured to be either RLD-left-right or ground-left-right electrodes that are configured to contact the skin of the user and measure a second high-fidelity biopotential signal;
   wherein the secondary smart band comprises a second microcontroller that digitizes the second high-fidelity biopotential signal to produce a second digitized signal and transmits the second digitized signal wirelessly to the primary smart band;
   wherein the primary smart band comprises a first microcontroller that wirelessly receives the second digitized signal from the secondary smart band, and also digitizes the first high-fidelity biopotential signal to produce a first digitized signal;
   wherein the first microcontroller employs DSP techniques on the first and second digitized signals to produce a high-fidelity ECG waveform signal; and
   wherein the primary smart band further comprises a D/A module to convert the second digitized signal to an analog signal; and a differential amplifier which receives as inputs the analog signal from the D/A module and the first high-fidelity biopotential signal and outputs a high-fidelity ECG waveform signal via analog signal conditioning and amplification.

2. The electrocardiogram monitor of claim 1 wherein the primary smart band and secondary smart band comprise separate power sources.

3. The electrocardiogram monitor of claim 1 wherein the primary smart band further comprises data storage for storing the ECG waveform signal and related information.

4. The electrocardiogram monitor of claim 1 wherein the primary smart band further comprises a transmitter for transmitting the ECG waveform signal and related information to a separate computing device.

5. The electrocardiogram monitor of claim 4 wherein the computing device is selected from one consisting of a mobile device, smartphone, tablet, laptop, and computer.

6. The electrocardiogram monitor of claim 1 wherein the primary smart band further comprises a display configured to display information to the user.

7. The electrocardiogram monitor of claim 6 wherein the information is selected from one or more of the group consisting of time, date, battery strength, wireless connectivity strength, Bluetooth status, HR, HRV, ECG waveform and alarm status.

8. The electrocardiogram monitor of claim 6 wherein the display is a touchscreen display that is configured to receive inputs from the user.

9. The electrocardiogram monitor of claim 1 wherein the primary smart band further comprises an alarm, wherein the first microcontroller computes HR and HRV data and triggers the alarm if the HR and/or HRV data are beyond pre-determined thresholds.

10. The electrocardiogram monitor of claim 1 wherein the smart bands are smartwatches.

11. The electrocardiogram monitor of claim 1 wherein the three electrodes include three rigid strip electrodes that are electrically connected to three flexible strip electrodes that are configured to maximize electrode contact area arounds the limbs and eliminate dependency on electrode position around a limb of the user to enhance signal quality.

12. The electrocardiogram monitor of claim 11 wherein the primary smart band and secondary smart band each have a rear face and straps; and wherein the three rigid strip electrodes are on the rear face of each of the primary and secondary smart bands and the three flexible strip electrodes are on the straps of each of the primary and secondary smart bands.

13. The electrocardiogram monitor of claim 12 further comprising a digital switch for each electrode to control which electrodes are in contact with the user.

14. The electrocardiogram monitor of claim 13 wherein the switches are used for reducing SNR to further improve ECG data quality and for testing and calibrating.

15. The electrocardiogram monitor of claim 1 further comprising a twin wireless charger for charging the primary smart band and secondary smart band.

16. The electrocardiogram monitor of claim 1 wherein the primary and secondary smart bands are configured to be attached at various locations along limbs of the user.

* * * * *